United States Patent [19]

Hara et al.

[11] 4,347,369
[45] Aug. 31, 1982

[54] 8-HYDROXY-HEXAHYDRONAPHTH[1',2':4,5]IMIDAZO[2,1-B]THIAZOLE AND ITS DERIVATIVES

[75] Inventors: Takeshi Hara, Hachioji; Yasutaka Kayama, Hino, both of Japan

[73] Assignee: Teijin Limited, Osaka, Japan

[21] Appl. No.: 202,383

[22] PCT Filed: Dec. 12, 1979

[86] PCT No.: PCT/JP79/00316
  § 371 Date: Aug. 15, 1980
  § 102(e) Date: Aug. 15, 1980

[87] PCT Pub. No.: WO80/01275
  PCT Pub. Date: Jun. 26, 1980

[30] Foreign Application Priority Data

Dec. 15, 1978 [JP] Japan .................. 53-154108

[51] Int. Cl.³ .................. A61K 31/425; C07D 513/04
[52] U.S. Cl. .................. 548/149; 424/270; 424/232; 548/305; 564/428
[58] Field of Search .................. 548/149

[56] References Cited

U.S. PATENT DOCUMENTS 3,954,784 5/1976 Acheson et al. .................. 548/149

FOREIGN PATENT DOCUMENTS 232976 12/1968 U.S.S.R. .................. 548/149

OTHER PUBLICATIONS

Knysh et al, Chemical Abstracts, vol. 76, Abstract No. 59209b (1972).
Radhakrishna et al, Chem. Abstracts, vol. 88, Abstract No. 136517y (1978).

*Primary Examiner*—Alton D. Rollins
*Attorney, Agent, or Firm*—Sughrue, Mion, Zinn, Macpeak & Seas

[57] ABSTRACT

Hexahydronaphth[1',2':4,5]imidazo[2,1-b]thiazole and its derivatives of formula [I]

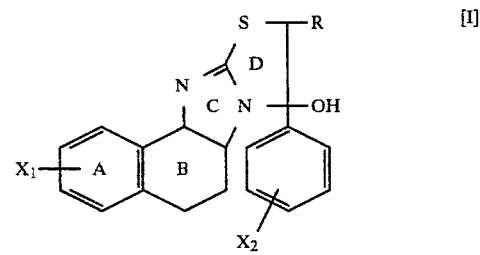

(where $X_1$ and $X_2$ stand for hydrogen or halogen atoms; R represents a hydrogen atom, lower alkyl of 1 to 4 carbon atoms or lower alkyl substituted with a carboxyl given as —$(CH_2)_n COOH$ (n is an integral number of 1 to 3); A, B, C, and D symbolize the rings respectively and the configuration of rings B and C is trans) and their acid adducts, and a method of preparing them according to the chemical equation given below:

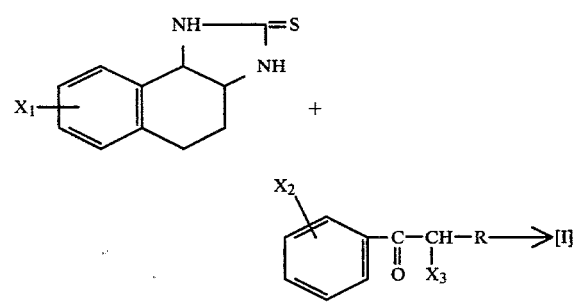

(where $X_3$ is a halogen atom). These compounds have immunostimulative activity.

3 Claims, No Drawings

8-HYDROXY-HEXAHYDRONAPHTH[1',2':4,5]IMIDAZO[2,1-B]THIAZOLE AND ITS DERIVATIVES

TECHNICAL FIELD

The present invention relates to novel compounds used as a medicine and veterinary drug and a method of preparing them. More particularly, the present invention relates to hexahydronaphth[1',2':4,5]imidazo[2,1-b]thiazole and its derivatives which are usable as a medicine for treating cancer or autoimmune diseases such as rheumatoid arthritis because of their immunostimulative and immunoregulative activities and as a veterinary anthelmintic and to a method of preparing them.

BACKGROUND ART

Tetramisole, or 2,3,5,6-tetrahydro-6-phenylimidazo[2,1-b]thiazole hydrochloride, is used as a veterinary anthelmintic and levamisol of formula (a) given below, that is, the levorotatory isomer of tetramisole, has immunostimulative and immunoregulative activities.

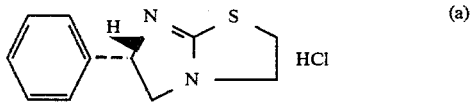
(a)

Much attention has been paid to these activities for application to immunotherapy for cancer and treatment for autoimmune diseases such as rheumatoid arthritis.

Further, 3-(p-chlorophenyl)-2,3-dihydro-3-hydroxy-thiazole[3,2-a]benzimidazole-2-acetic acid (NSC 208828), which has a chemical structure similar to levamisol as shown in formula (b), also has been known to have immunostimulative and carcinostatic activities. Although these activities are

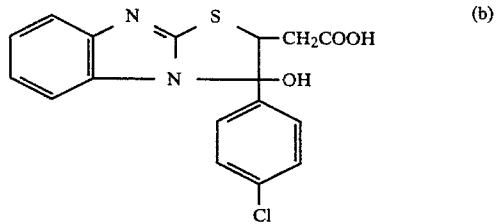
(b)

lower than in levamisole, its low toxicity has received considerable attention.

Their pharmaceutical effect, toxicity, etc., have yet to be elucidated definitely and thorough investigation has been expected on these compounds and their analogs with similar structure.

The present inventors, in an effort to find compounds having better immunostimulative and immunoregulative activities as compared with these known compounds aforementioned, have synthesized many kinds of novel compounds with basic structures analogous to that of the known compounds mentioned above, studied the pharmaceutical properties, and have come to achieve the present invention.

DISCLOSURE OF INVENTION

The present invention relates to hexahydronaphth[1',2':4,5]imidazo[2,1-b]thiazole and its derivatives which are shown as formula [I]

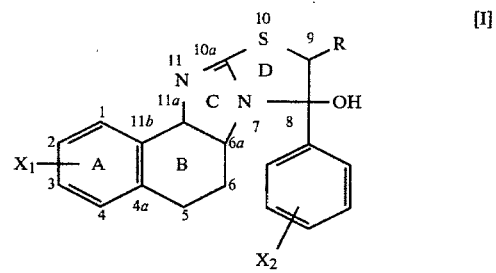
[I]

(where $X_1$ and $X_2$ stand for hydrogen and halogen atoms; R represents a hydrogen atom, lower alkyl of 1 to 4 carbon atoms or carboxyl-substituted lower alkyl given as $HOOC(CH_2)_n$—(n is an integral number of 1 to 3); A, B, C, and D symbolize the rings respectively and the configuration of rings B and C is trans).

According to the present invention, hexahydronaphth[1',2':4,5]imidazo[2,1-b]thiazole and its derivatives of formula [I] are prepared by reaction of tetrahydronaphthimidazoline-2-thiones (3a,4,5,9a-tetrahydronaphth[1,2-d]imidazoline-2-thione and its derivatives) of formula [II]

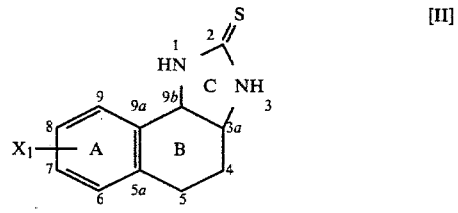
[II]

(where X represents a hydrogen or halogen atom; A, B, and C symbolize the rings respectively; the configuration of rings B and C is trans) with α-haloketones of formula [III]

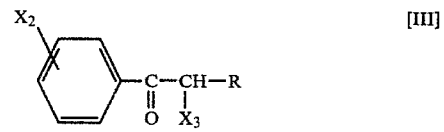
[III]

(where $X_2$ represents a hydrogen or halogen atom; $X_3$ stands for a halogen atom; and R represents a hydrogen atom, lower alkyl of 1 to 4 carbon atoms, or carboxyl-substituted lower alkyl given as $—(CH_2)_nCOOH$ (n is an integral number of 1 to 3)).

Best Mode of Carrying out the Invention

In formula [I] described above, $X_1$ and $X_2$ are hydrogen or halogen atoms, in which the halogen is preferably fluorine, chlorine or bromine. The position and number of the halogen substitution are not restricted in particular. R is a hydrogen atom, lower alkyl of 1 to 4 carbon atoms or carboxyl-substituted lower alkyl given as $—(CH_2)_nCOOH$ (n is an integral number of 1 to 3) and especially a hydrogen atom, methyl, and carboxymethyl are preferred.

In the present invention, the configuration of rings B and C is trans-form. The synthesis of derivatives with cis-form in rings B and C is very difficult due to the steric hindrance of the phenyl group in the 8-position of formula [I]. The configuration of the substituents in the 8- and 9-positions is not restricted in particular in the present invention.

In the present invention, the hexahydronaphth[1',2':4,5]imidazo[2,1-b]thiazole derivatives may be also in the form of the salt adduct with an inorganic or organic acid. The inorganic acid used is, for example, hydrochloric, hydrobromic, hydroiodic, sulfuric or phosphoric acid. The organic acid is, for example, acetic, propionic, glycolic, lactic, pyruvic, oxalic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic or salicylic acid.

According to the present invention, the reaction of a tetrahydronaphthimidazoline-2-thione of formula [II] given above in which the configuration of rings B and C is trans with an α-haloketone of formula [III] affords a hexahydronaphth[1',2':4,5] imidazo[2,1-b]thiazole derivative of formula [I]. The definitions of $X_1$ in formula [II] and $X_2$ and R in formula [III] are the same as in formula [I]. Further, $X_3$ is formula [III] represents a halogen, and chlorine or bromine is preferred.

The resultant hexahydronaphth[1',2':4,5]-imidazo[2,1-b]thiazole derivative is expected to be a mixture of 4 stereoisomers when the configurations in the 8- and 9-positions are taken into consideration (2 isomers when R is a hydrogen atom), wherein the optical isomers are not taken into account, but some substituents cause the predominant formation of specific isomers. The reaction mixture is subjected to, for example, extraction, chromatography, recrystallization, etc., and divided into each stereoisomer.

The hexahydronaphth[1',2':4,5]imidazo[2,1-b]thiazole derivatives in the present invention mean the stereoisomers and their mixtures aforementioned.

In the reaction between the compounds of formula [II] and [III], 1 to 10 moles of an α-haloketone are preferably used to 1 mole of a tetrahydronaphth[1,2-d]imidazoline-2-thione. Usually, the reaction is effected using an appropriate solvent. As the solvent, any substance may be employed if it does not hinder the reaction and preferable solvents are as follows: alcohols such as ethanol, n-propanol, isopropanol, n-butanol, etc.; carboxylic acids, acetic, n-propionic acid, etc.; acetonitrile, N,N-dimethylformamide, etc. These solvents may be used in the form of mixture consisting of 2 and more kinds. The optimum reaction temperature depends on the solvent employed and is suitably selected from room temperature to the boiling point of the reaction system. The reaction time depends upon the reactants, reaction scale, solvent and reaction temperature used; however, it is usually about 30 minutes to 48 hours.

The hexahydronaphth[1',2':4,5]imidazo[2,1-b]thiazole derivatives of formula [I] obtained according to the present invention can be isolated and purified from the reaction mixture by such usual operations as filtration, extraction, recrystallization, chromatography, etc.

Further, the reaction of a tetrahydronaphth[1,2-d]imidazoline-2-thione of formula [II] and an α-haloketone of formula [III] gives a hydrohalide salt adduct of hexahydronaphth[1',2':4,5]imidazo[2,1-b]thiazole derivative as the first product. After isolation or directly without isolation, the product is treated with an aqueous ammonia, sodium bicarbonate, sodium carbonate, sodium hydroxide, etc., to remove the hydrogen halide in the form of a salt with one of these bases, thus producing the compound of formula [I].

When necessary, the hexhydronaphth[1',2':4,5]imidazole[2,1-b]thiazole derivatives may be isolated in the form of the acid adduct with an inorganic or organic acid aforementioned. Or after being isolated as a free base, the derivatives may be converted into the acid adduct by treating with an adequate inorganic or organic acid.

The tetrahydronaphthimidazoline-2-thione of formula [II] given above is prepared by reaction of one of the compounds of formula [d] given below:

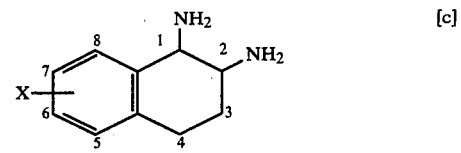

(where $X_1$ represents a hydrogen or halogen atom) namely 1,2-diamino-1,2,3,4-tetrahydronaphthalene and its derivative, with carbon disulfide, followed by dehydrosulfurization. In the compounds of formula [c], the configuration of the two amino groups is trans-form.

The 1,2-diamino-1,2,3,4-tetrahydronaphthalene and its derivatives of formula [c] are made by a variety of methods. For example, they are obtained from a 2-halo-3,4-dihydro-1(2H)-naphthalenone that is readily derived from 3,4-dihydro-1(2H)-naphthalenone by the method that Koptyug et al. have described in Zhurnal Obshchei Khimii, 32 1613 (1962) or from a 1,2-dihydronaphthalene that is derived from 3,4-dihydro-1(2H)-naphthalenone by the method that Swift et al. have described in Journal of Organic Chemistry 32 511 (1967).

Further, the α-haloketones of formula [III] is obtained by halogenation of a ketone of formula [d]

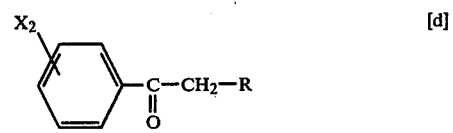

(where $X_2$ represents a hydrogen or halogen atom; R stands for a hydrogen atom, lower alkyl of 1 to 4 carbon atoms, or carboxyl-substituted lower alkyl (n is an integer of 1 to 3)) according to a known method.

The present invention is illustrated for further detail but not limited by the following Examples.

EXAMPLE 1:

(1) Preparation of trans-3a,4,5,9b-tetrahydronaphth[1,2-d]imidazoline-2-thione

Trans-1,2-diamino-1,2,3,4-tetrahydronaphthalene (461 mg, 2.84 m mol) was dissolved in ethanol (8 ml), water (4 ml) was added to the solution, then carbon disulfide (190 μl, 3.17 m mol) was added thereto under stirring at room temperature. The mixture was heated under reflux for 4 hours and cooled in an ice-water bath. The crystals precipitating out were separated by filtration, washed with ether and dried in vacuum to give trans-3a,4,5,9b-tetrahydronaphth[1,2-d]imidazoline-2-thione (350 mg, 1.71 m mol) in 60% yield. The data spectroscopy and elemental analysis were as follows:

IR(KBr)cm$^{-1}$: 3170, 2950, 2880, 1508, 1458, 1429, 1337, 1330, 1235, 1218, 1197, 1177, 1157, 1126, 1110, 742, 713, 689.

NMR (COCl$_3$:DMSO-d$_6$=3:2), δ from TMS in ppm: 1.63–2.64 (2H, m, CH$_2$ in the 4-position); 2.90–3.67 (3H, m, CH in the 3a-position and CH$_2$ in the 5-position); 4.42 (1H, d, J=13 Hz, CH in the 9b-position); 7.13–7.50 (4H, m, H on the benzene ring); 8.47 (1H, broad s, NH); 9.08 (1H, borad s, NH).

Elemental analysis (C$_{11}$H$_{12}$N$_2$S) Calculated: C, 64.67; H, 5.92; N, 13.71%. Found: C, 64.40; H, 5.74; N, 13.61%.

(2) Preparation of 6a,11a-trans-5,6,6a,8,9,11a-hexahydro-8-hydroxy-9-methyl-8-phenylnaphth[1',2':4,5]imidazo[2,1-b]thiazole hydrobromide The trans-3a,4,5,9b-tetrahydronaphth[1,2-d]imidazoline-2-thione resulting from (1) (200 mg, 0.979 m mol) was dissolved in N,N-dimethylformamide (1 mol), α-bromopropiophenone (235 mg, 1.10 m mol) was added to the solution, and they were stirred at room temperature for 21 hours.

Ether (8 ml) was added to the reaction mixture and they were stirred for 1 hour. The colorless solid formed was separated by filtration, washed with ether and dried to give 6a,11a-trans-5,6; 6a,8,9,11a-hexahydro-8-hydroxy-9-methyl-9-phenylnaphth[1',2':4,5]imidazo[2,1-b]thiazole hydrobromide (345 mg) in 84% yield. The product gave the following data on spectroscopy and was found to be a mixture of 2 kinds of stereoisomers caused by substituents in the 8- and 9-positions.

IR(KBr)cm$^{-1}$: 3100, 3030 (shoulder), 2930 (shoulder), 2880, 2820 (shoulder), 1540–1520, 1448, 1304, 1230, 750.

NMR (DMSO-do), δ from TMS in ppm: 1.02 and 1.38 (3H, d, J=7 Hz, CH$_3$); 1.3–1.8 (2H, m, CH$_2$ in the 6-position); 2.73–3.04 (2H, m, CH$_2$ in the 5-position); 3.6–4.15 (1H, m, CH in the 6a-position); 4.52–4.65 (1H, g, J=7 Hz, CHCH$_3$), 5.51–5.64 (1H, d, J=14 Hz, CH in the 11a-position); 7.19–8.04 (9H, m, H in the 1,4-positions and on C$_6$H$_5$).

(3) Preparation of 6a,11a-trans-5,6,6a,8,9,11a-hexahydro-8-hydroxy-9-methyl-8-phenylnaphth[1',2':4,5]imidazo[2,1-b]thiazole.

The 6a,11a-trans-5,6,6a,8,9,11a-hexahydro-8-hydroxy-9-methyl-8-phenylnaphth[1',2':4,5]imidazo[2,1-b]thiazole hydrobromide obtained in (2) (200 mg) was suspended in methylene chloride (6 ml). The suspension was made basic by adding conc. aqueous ammonia and separated into two layers. The organic layer was washed with aqueous sodium chloride and dried over anhydrous sodium sulfate, then the solvent was distilled off under reduced pressure. The residue was crystallized out by adding ether (6 ml) and separated by filtration to give 6a, 11a-trans-5,6,6a,8,9,-11a-hexahydro-8-hydroxy-9-methyl-8-phenyl-naphth[1',2':4,5]imidazo[2,1-b[thiazole as colorless solid (142 mg). The product gave the following data on spectroscopy.

NMR (CDCl$_3$), δ from TMS in ppm: 1.04 and 1.63 (3H, d, J=7 Hz, CH$_3$); 1.1–1.9 (2H, m, CH$_2$ in the 6-position); 2.5–2.9 (2H, m, CH$_2$ in the 5-position); 3.1–3.7 (1H, m, CH in the 6a-position); 3.82 and 4.22 (1H, g, J=7 Hz, CHCH$_3$); 4.80 and 4.98 (1H, d, J=13 Hz, CH in the 11a position); 6.89–7.90 (9H, m, H in the 1-4 positions and on C$_6$H$_5$).

(4) Resolution of 6a,11a-trans-5,6,6a,8,9,11a-hexahydro-8-hydroxy-9-methyl-8-phenylnaphth[1',2':4,5]imidazo[2,1-b]thiazole The recrystallizaton of the 6a,11a-trans-5,6,6a,8,9,-11a-hexahydro-8-hydroxy-9-methyl-8-phenyl-naphth[1',2':4,5]imidazo[2,1-b]thiazole obtained in (3) (a mixture of 2 kinds of stereoisomers) was repeated from methylene chloride to provide the stereoisomer in the 8- and 9-positions in pure form as colorless needles, mp 177° C. The compound showed the following data on spectroscopy.

IR(KBr)cm$^{-1}$: 1581, 1562, 1488, 1450, 1426, 1207, 1198, 1177, 1164, 1151, 745, 708.

NMR (DMSO-d$_6$), δ from TMS in ppm: 1.19 (3H, d, J=7Hz, CH$_3$); 1.10–1.80 (2H, m, CH$_2$ in the 6-position); 2.41–3.50 (3H, m, CH in the 6a-position and CH$_2$ in the 5-position); 4.17 (1H, g, J=7Hz, CHCH$_3$); 4.73 (1H, d, J=13Hz, CH in the 11a-position); 6.83 (1H, s, OH); 7.05–7.82 (9H, m, H in the 1-4 positions and C$_6$H$_5$).

Elemental analysis (C$_{20}$H$_{20}$N$_2$OS) Calculated: C, 71.40; H, 5.99; N, 8.33%. Found: C, 71.28; H, 5.80; N, 8.17%.

EXAMPLE 2

(1) Preparation of 6a,11a-trans-5,6,6a,8,9,11a-hexahydro-8-hydroxy-8-phenylnaphth[1',2':4,5]imidazo[2,1-b]thiazole hydrobromide Trans-3a,4,5,9b-tetrahydronaphth[1,2-d]imidazoline-2-thione (200 mg, 0.979 m mol) was dissolved in N,N-dimethyl formamide (1.5 ml) and the solution was combined with phenacyl bromide (220 mg, 1.11 m mol) and stirred for 27 hours at room temperature. Ether (10 ml) was added to the reaction mixture and stirring was continued additionally for 2 hours. The solid formed was separated by filtration, washed with N,N-dimethyl-formamideether and dried to give 6a,11a-trans-5,6,6a,8,9,11a-hexahydro-8-hydroxy-8-phenyl-naphth[1',2':4,5]imidazo[2,1-b]thiazole hydrobromide (379 mg) in 99% yield.

The product showed the following data on spectroscopy.

IR(KBr) in cm$^{-1}$: 3150, 2900, 1545, 1453, 1179, 1164, 1059, 749.

(2) Preparation of 6a,11a,-trans-5,6,6a,8,9,11a-hexahydro-8-hydroxy-8-phenylnaphth[1',2':4,5]imidazo[2,1-b]thiazole The 6a,11a-trans-5,6,6a,8,9,11a-hexahydro-8-hydroxy-8-phenylnaphth[1',2':4,5]imidazo[2,1-b]thiazole hydrobromide (333 mg) obtained in (1) was suspended in methylene chloride (20 ml), the suspension was shaken with 5% aqueous ammonia (10 ml) and separated into two layers. The organic layer was washed with aqueous sodium chloride and dried over anhydrous sodium sulfate. The solvent was distilled off under reduced pressure and a colorless solid of 6a, 11a,-trans-5,6,6a,8,9,11a-hexahydro-8-hydroxy-8-phenyl-naphth[1',2':4,5]imidazo[2,1-b]thiazole (244 mg) was obtained. The recrystallization from methylene chloride gave colorless prisms melting at 151° to 152° C. The data on spectroscopy were as follows:

IR(KBr)cm$^{-1}$: 1585, 1568, 1488, 1452, 1426, 1200, 1186, 1010, 745, 694.

NMR (DMSO-d$_6$), δ from TMS in ppm: 1.1–1.9 (2H, m, CH$_2$ in the 6-position); 2.6–3.6 (3H, m, CH in the 6-position and CH$_2$ in the 5-position); 3.66 and 3.82 (2H, AB-system, J=1.16Hz, S-CH$_2$); 4.88 (1H, d, J=12.8Hz, CH in the 11a-position); 6.85 (1H, s, OH); 7.05–7.83 (9H, m, H in the 1–4-positions and on C$_6$H$_5$);

EXAMPLE 3

Preparation of
6a,11a,-trans-9-carboxymethyl-8-(4-chlorophenyl)-5,6,6a,8,9,11a-hexahydro-8-hydroxynaphth[1′,2′:4,5]imidazo[2,1-b]thiazole hydrobromide Trans-3a,4,5,9b-tetrahydronaphth[1,2-d]imidazoline-2-thione (245 mg, 1.20 m mol) was suspended in acetic acid (5.0 ml), combined with 3-bromo-3-(4-chlorobenzoyl) propionic acid (354 mg, 1.21 m mol) and they were stirred on an oil bath at 90° C. for 90 minutes. After the acetic acid was distilled off under reduced pressure, ether (10 ml) was added to the residue to give 6a,11a-trans-9-carboxymethyl-8-(4-chlorophenyl)-5,6,6a,8,9,-11a-hexahydro-8-hydroxynaphth[1′,2′:4,5]imidazo[2,1-b]thiazole hydrobromide (446 mg) in 76% yield. The product was recrystallized out of methanol-acetonitrile to afford colorless needles melting 214.5° to 215.5° C. (decomposition). Data on spectroscopy and elemental analysis were as follows:

IR(KBr) in cm$^{-1}$: 3210, 2940, 1729, 1544, 1490, 1451, 1400, 1348, 1230, 1210, 1160, 1147, 1095.

NMR (DMSO-d$_6$), δ from TMS in ppm: 1.13–2.17 (2H, m, CH$_2$ in the 6-position); 2.69–3.07 (4H, m, CH$_2$ in the 5-position and CH$_2$CO$_2$H); 3.53–4.03 (1H, m, CH in the 6a-position); 4.62–4.87 (1H, m, SCH); 5.45 (1H, d, J=14Hz, CH in the 11a-position); 7.17–8.10 (10H, m, H on the aromatic rings CO$_2$H and N-H).

Elemental Analyses (C$_{21}$H$_{20}$N$_2$BrClO$_3$S): Calculated: C, 50.87; H, 4.07; N, 5.65%. Found: C, 50.99; H, 4.07; N, 5.68%.

EXAMPLE 4

(1) Preparation of
trans-7-chloro-3a,4,5,9b-tetrahydronaphth[1,2-d]imidazoline-2-thione:

Trans-1,2-diamino-6-chloro-1,2,3,4-tetrahydronaphthalene (5.14 g, 26.1 m mol) was dissolved in ethanol (60 ml) and kept at room temperature under a nitrogen atmosphere. The solution was stirred and carbon disulfide (1.70 ml, 28.4 m mol) was added. About 1 minute after the addition, solid precipitated. The stirring was continued for an additional 10 minutes at room temperature, then water (30 ml) was added and the mixture was heated under refluxing for 2.5 hours. The reaction mixture was cooled on an ice bath for 1 hour and the solid precipitate was collected by filtration. The precipitate was washed with about 150 ml of a water, further with 20 ml of ether-n-hexane mixture (volume ratio; 1:2) and 40 ml of n-hexane in turn and dried under vacuum over night to give trans-7-chloro-3a,4,5,9b-tetrahydronaphth]1,2-d]imidazoline-2-thione (4.86 g, 20.4 m mol) in 78% yield. The product was recrystallized from methanol-acetonitrile to give colorless prisms melting at 269°–271° C. (decomposed). The data on spectroscopy and elemental analysis were as follows:

IR (KBr) in cm$^{-1}$: 3160, 2930, 2870, 1600, 1515, 1485, 1337, 1228, 1196, 1176, 1147, 1089, 881, 823, 792, 682.

NMR (DMSO-d$_6$), δ from TMS in ppm: 1.60–2.30 (2H, m, CH$_2$ in the 4-position); 2.87–3.17 (2H, m, CH$_2$ in the 5-position); 3.32–3.59 (1H, m, CH in the 3a-position); 4.83 (1H, d, J=13Hz, CH in the 9b-position); 7.17–7.50 (3H, m, H on benzene ring); 8.73 (1H, broad s, NH); 9.18 (1H, broad s, NH).

Elemental Analysis (C$_{11}$H$_{11}$ClN$_2$S) Calculated: C, 55.34; H, 4.64; N, 11.73%. Found: C, 55.33; H, 4.49; N, 11.89%.

(2) Preparation of
6a,11a-trans-9-carboxymethyl-3-chloro-5,6,6a,8,9,11a-hexahydro-8-hydroxy-8-phenylnaphth[1,2′:4,-5]imidazo[2,1-b]thiazole hydrobromide A mixture of trans-7-chloro-3a,4,5,9b-tetrahydronaphth[1,2-d]imidazoline-2-thione (300 mg, 1.26 m mol) 3-benzoyl-3-bromopropioic acid (325 mg, 1.26 m mol) in acetic acid (5 ml) was heated at 90° C. on an oil bath with stirring under a nitrogen atmosphere for 1 hour. The solvent was distilled off under reduced pressure, ether (15 ml) was added to the residue, and they were stirred at room temperature for 1 hour. The solid was filtered by sucking, rinsed with ether and dried under reduced pressure to give 6a,11a-trans-9-carboxymethyl-3-chloro-5,6,6a,8,9,11a-hexahydro-8-hydroxy-8-phenylnaphth[1′,2′:4,5]imidazo[2,1-b]thiazole hydrobromide (372 mg, 0.75 m mol) in 60% yield. The product was recrystallized from methanol-benzene to give needles melting at 218° to 223° C. (decomposition). The needles showed the following data on spectrocopy and elemental analysis.

IR(KBr) in cm$^{-1}$: 3200, 3100, 3050, 2970, 2920, 1721, 1543, 1470, 1407, 1185, 1176, 1158, 1150.

NMR (DMSO-d$_6$), δ from TMS in ppm: 1.22–2.21 (2H, m, CH$_2$ in the 6-position); 2.75–3.04 (4H, m, CH$_2$ in the 5-position and —CH$_2$COOH in the 9-position); 3.57–4.16 (1H, m, CH in the 6-position); 4.82 (1H, dd, J=11Hz, 5Hz, SCH); 5.52 (1H, d, J=14Hz, CH in the 11a-position); 7.36–8.13 (10H, m, H in the 1–4 positions, H on the aromatic ring, OH and CO$_2$H).

Elemental Analysis (C$_{21}$H$_{20}$BrClN$_2$O$_3$S): Calculated: C, 50.87, H, 4.07; N, 5.65%. Found: C, 50.93; H, 4.20; N, 5.72%.

EXAMPLE 5

Preparation of
6a,11a-trans-9-carboxymethyl-3-chloro-8-(4-chlorophenyl)-5,6,6a,8,9,11a-hexahydro-8-hydroxynaphth[1′,2′:4,5]imidazo[2,1-b]thiazole hydrobromide A mixture of trans-7-chloro-3a,4,5,9b-tetrahydronaphth[1,2-d]imidazoline-2-thione (234 mg, 9.80 m mol) and 3-chloro-3-(4-chlorobenzoyl)propioic acid (286 mg, 0.981 m mol) in acetic acid (5 ml) was heated under reflux for 2 hours. In the course of the reaction, the mixture once formed a solution and then precipitated crystals again. Most of the acetic acid was distilled off under reduced pressure, ether (20 ml) was added to the residue and they were stirred at room temperature for 2 hours. The solid was filtered with suction, washed with ether and dried under reduced pressure to give 6a,11a-trans-9-carboxymethyl-3-chloro-8-(4-chlorophenyl)-5,6,6a,8,9,11a-hexahydro-8-hydroxynaphth[1′,2′:4,5]imidazo[2,1-b]thiazole hydrobromide of substantially colorless crystals (372 mg) in 72% yield. The product was recrystallized from methanol-acetonitrile to give needles melting at 250°–255° C. (decomposition). The data on spectroscopy and elemental analysis were as follows:

IR(KBr) in cm$^{-1}$: 3200, 3060, 2960, 1720, 1531, 1476, 1405, 1237, 1229, 1160, 1149, 1096, 829.

NMR (DMSO-d$_6$) δ from TMS in ppm: 1.24–2.23 (2H, m, CH$_2$ in the 6-position); 2.64–3.26 (4H, m, CH$_2$ in the 5-position, —CH$_2$COOH in the 9-position); 3.83 (1H, m CH in the 6a-position); 4.78 (1H, dd, J=10Hz, 5Hz, SCH in the 9-position); 5.47 (1H, d, 14Hz, CH in the 11a-position); 1.33–8.40 (9H, m, H on the benzene ring, OH, CO$_2$H).

Elemental Analysis (C$_{21}$H$_{19}$BrCl$_2$N$_2$O$_3$S) Calculated: C, 4757; H, 3.61; N, 5.28%. Found: C, 47.45; H, 3.73; N, 5.35%.

EXAMPLE 6

(1) Preparation of trans-7-fluoro-3a,4,5,9b-tetrahydronaphth[1,2-d]imidazoline-2-thione Trans-1,2-diamino-6-fluoro-1,2,3,4-tetrahydronaphthalene (3.84 g, 21.3 m mol) was dissolved in ethanol (40 ml) and carbon disulfide (1.4 ml, 23.4 m mol) was added to the solution. After the resulting white suspension was stirred for a while, water (20 ml) was added to the suspension and they were heated under reflux for 30 minutes. The reaction mixture was cooled with ice and the precipitate was filtered. The solid was washed in turn with water (three portions of 20 ml, totaling 60 ml), ethyl ether (20 ml) and n-hexane (50 ml) and dried under vacuum to give trans-7-fluoro-3a,4,5,9b-tetrahydronaphth[1,2-d]imidazoline-2-thione as a yellowish grey solid (3.88 g, 17.4 m mol) in 82% yield. The product was recrystallized from acetone-acetonitrile to give light-yellow needles melting at 256.5° to 257.5° C. (decomposition). The data on spectroscopy were as follows:

IR(KBr) in cm$^{-1}$: 3430, 3165, 1620, 1501, 1437, 1422, 1337, 1252, 1230, 1208, 1193, 1158, 1100, 878, 857, 802, 731, 708, 689.

NMR (DMSO-d$_6$), δ from TMS in ppm: 1.63–2.27 (2H, m, CH$_2$ in the 4-position); 2.87–3.57 (3H, m, CH$_2$ in the 5-position, CH in the 3a-position); 4.35 (1H, d, J=1.2Hz, CH in the 9b-position); 6.83–7.51 (3H, m, H on the benzene ring); 8.66 (1H, broad s, NH); 9.13 (1H, broad s, NH).

(2) Preparation of 6a,11a-trans-9-carboxymethyl-3-fluoro-5,6,6a,8,9,11a-hexahydro-8-hydroxy-8-phenylnaphth[1',2':4,5]imidazo[2,1-b]thiazole hydrobromide Trans-7-fluoro-3a,4,5,9b-tetrahydro[1,2-d]imidazoline-2-thione (300 mg, 1.35 m mol) was suspended in acetic acid (6 ml), 3-benzoyl-3-bromopropionic acid (350 mg, 1.36 m mol) was added, and they were stirred at 90° C. on an oil bath for 45 minutes. After the acetic acid was distilled off under reduced pressure, ethyl ether (10 ml) was added, and the solid was filtered, whereby 6a,11a-trans-9-carboxymethyl-3-fluoro-5,6,6a,8,9,11a-hexahydro-8-hydroxy-8-phenyl-naphth[1',2':4,5]imidazo [2,1-b]thiazole hydromide (511 mg) was obtained as a white solid in 79% yield. The product was recrystallized from methanol-ethyl acetate to give colorless needles melting at 208°–221° C. The product gave the following data on spectroscopy.

IR(KBr) in cm$^{-1}$: 3405, 3070, 1711, 1621, 1536, 1496, 1453, 1404, 1254, 1151.

NMR (DMSO-d$_6$), δ from TMS in ppm: 1.17–2.14 (2H, m, CH$_2$ in the 6-position); 2.70–3.00 (4H, m, CH$_2$ in the 5-position and CH$_2$C$_2$H); 3.56–4.07 (1H, m, CH in the 6a-position); 4.63–4.89 (1H, m, SCH); 5.45 (1H, d, J=14Hz, CH in the 11a-position); 6.98–8.13 (10H, m, H on the aromatic ring, CO$_2$H and N–H).

EXAMPLE 7

(1) Preparation of 6a,11a-trans-9-carboxymethyl-8-(4-chlorophenyl)-3-fluoro-5,6,6a,8,9,11a-hexahydro-8-hydroxynaphth[1',2':4,5]imidazo[2,1-b]thiazole hydrobromide Trans-7-fluoro-3a,4,5,9b-tetrahydro[1,2-d]imidazoline-2-thione (250 mg, 1.12 m mol) was suspended in acetic acid (5 ml), 3-bromo-3-(4-chlorobenzoyl)-propioic acid (330 mg, 1.13 m mol) was added thereto, and they were stirred on an oil bath heated to 90° C. for 2 hours and 50 minutes. After acetic acid was distilled off under reduced pressure, ethyl ether (10 ml) was added to the residue and 6a,11a-trans-9-carboxymethyl-8-(4-chlorophenyl)-3-fluoro-5,6,6a,8,9,11a-hexahydro-8-hydroxynaphth[1',2':4,5]imidazo[2,1-b]thiazole hydrobromide (495 mg, 0.963 m mol) was obtained by filtration as a white solid in 86% yield. The product was recrystallized from methanol-benzene and subsequently from methanol-ethyl acetate to afford colorless needles melting at 226° to 230° C. The data on spectroscopy were as follows:

IR(KBr) in cm$^{-1}$: 3410, 3190, 2960, 1711, 1611, 1533, 1492, 1405, 1253, 1150, 1098.

NMR [DMSO-d$_6$ -CD$_3$OD (2:1)], δ from TMS in ppm: 1.31–2.02 (2H, m, CH$_2$ in the 6-position); 2.80–3.03 (4H, m, CH$_2$ in the 5-position and CH$_2$COOH); 3.60–4.11 (1H, m, CH in the 6a-position); 4.83 (1H, dd, J=11Hz, 5Hz, SCH); 5.48 (1H, d, J=15Hz, CH in the 11a-position); 6.99–7.96 (7H, m, H on aromatic ring).

EXAMPLE 8

(1) Preparation of trans-8-bromo-3a,4,5,9b-tetrahydronaphth[1,2-d]imidazoline-2-thione Trans-1,2-diamino-7-bromo-1,2,3,4-tetrahydronaphthalene (6.75 g, 28.0 m mol) was dissolved in ethanol (70 ml) and carbon disulfide (1.9 ml, 31.7 m mol) was added to the solution. After stirring at room temperature for 20 minutes, they were heated under reflux for 5.5 hours. The reaction mixture was cooled in an ice bath and crystals precipitated were collected by filtration, whereby trans-8-bromo-3a,4,5,9b-tetrahydronaphth[1,2-d]imidazoline-2-thione (5.57 g) was obtained in 70% yield. The crystals were recrystallized from methanol-acetonitrile to give pale-yellow crystals melting at 259.5°–260.5° C. (decomposition). The product gave the following data on spectroscopy and elemental analysis.

IR(KBr) in cm$^{-1}$: 3145, 1501, 1483, 1420, 1337, 1234, 1191, 1156, 1105.

NMR (DMSO-d$_6$), δ from TMS in ppm: 1.63–2.30 (2H, m, CH$_2$ in the 4-position); 2.83–3.19 (2H, m, CH$_2$ in the 5-position); 3.33–3.83 (1H, m, CH in the 3a-position); 4.44 (1H, d, J=13Hz, CH in the 9b-position); 7.16 (1H, d, J=8Hz, CH in the 6a-position); 7.45 (1H, dd, J=8Hz, 2Hz, H in the 7-position); 7.65 (1H, d, J=2Hz, H in the 9-position); 8.73 (1H, s, NH); 9.12 (1H, s, NH).

Elemental Analysis (C$_{11}$H$_{11}$BrN$_2$S): Calculated: C, 46.66; H, 3.92; N, 9.89%. Found: C, 46.60; H, 3.84; N, 9.90%.

(2) Preparation of 6a,11a-trans-2-bromo-9-carboxymethyl-8-(4-chlorophenyl)-5,6,6a,8,9,11a-hexahydro-8-hydroxynaphth[1′2,2′:4,5]imidazo[2,1-b]thiazole hydrobromide Trans-8-bromo-3a,4,5,9b-tetrahydronaphth[1,2-d]imidazoline-2-thione (250 mg, 0.883 m mol) was suspended in acetic acid (5 ml) and 3-bromo-3-(4-chlorobenzoyl) propionic acid (260 mg, 0.892 m mol) was added to the suspension and they were stirred on an oil bath heated to 80° C. for 55 minutes. After the acetic acid was distilled off under reduced pressure, ether (10 ml) was added to the residue to give 6a,11a-trans-2-bromo-9-carboxymethyl-8-(4-chlorophenyl)-5,6,6a,8,9,-11a-hexahydro-8-hydroxynaphth[1′,2′:4,5]imidazo[2,1-b]thiazole hydrobromide of pale yellow (398 mg) in 78% yield. The product was recrystallized from methanol-benzene to afford colorless powdery crystals melting at 208.5–215° C.

The data on spectroscopy were as follows:

IR(KBr) in cm$^{-1}$: 3390, 3080, 2950, 1714, 1542, 1488, 1400, 1358, 1309, 1236, 1175, 1093.

NMR (DMSO-d$_6$), δ from TMS in ppm: 1.32–2.07 (2H, m, CH$_2$ in the 6-position); 2.62–3.10 (5H, m, CH$_2$ in the 5-position, CH$_2$CO$_2$H and CH in the 6a-position); 4.62–4.90 (1H, m, SCH); 5.49 (1H, d, J=14Hz, CH in the 11a-position); 7.07–7.90 (9H, m, H on aromatic ring, OH and CO$_2$H); 8.02–8.28 (1H, m, N-H).

EXAMPLE 9

This example shows the immunostimulative activity of hexahydro[1′,2′:4,5]imidazo[2,1-b]thiazole derivatives which were prepared in examples 1–8.

(1) E effect on humoral antibody formation

Experiment-1: ICR mice (male, 8-weeks old) or CDF$_1$ mice (male, 8-weeks old) were administered intraperitoneally with 10$^8$ sheep red blood cells as an antigen and, 24 hours after the administration, the respective drugs were likewise administered intraperitoneally. Four days after the administration of the antigen, antibody-forming cells in the spleens of the mice were counted according to the method of A. J. Cunningham and A. Czenberg [see the Immunology, 14 599–600 (1969)].

For the purpose of comparison, experiments were also conducted with the mice which were not administered with the drugs and with those administered with known levamisole instead of the drugs according to the present invention. The results of these experiments are shown in Table-1 in which the results obtained with the ICR mice are given in Experiment-1a and those obtained with the CDF$_1$ mice are given in Experiment-1b.

Experiment-2: C3H/He mice (male, 17-weeks old) were administered intravenously with 5×10$^5$ sheep red blood cells as an antigen and, 24 hours after the administration of antigen, the respective drugs were administered subcutaneously in the inguinial region of the mice. Four days after the administration of antigen, antibody-forming cells in the spleens of the mice were counted according to the same method as adopted in Experiment-1. As in the case of Experiment-1, experiments with no use of the drugs and with the use of levamisol also were conducted for the purpose of comparison. The results of these experiments are shown in Table-1.

TABLE 1

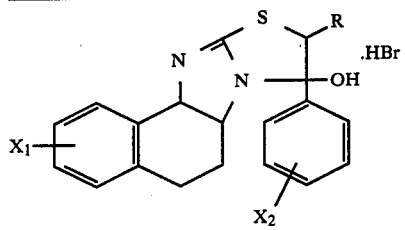

| | Dosage (mg/mouse) | No. of antibody-forming cells/10$^6$spleen cells | | |
|---|---|---|---|---|
| | | Experiment-1a | Experiment-1b | Experiment 2 |
| No drug | | 560 ± 100 | 1100 ± 125 | 3290 ± 70 |
| Levamisole | 0.1 | 565 ± 120 | 940 ± 60 | 4100 ± 190 |
| | 0.4 | 1200 ± 150 | 1320 ± 150 | 3180 ± 120 |
| X$_1$ = H, X$_2$ = H, R = CH$_3$ | 0.1 | 550 ± 70 | — | — |
| [Example 1-(2)] | 0.4 | 1120 ± 260 | | |
| X$_1$ = H, X$_2$ = p-Cl, R = CH$_2$COOH | 0.1 | 510 ± 130 | — | — |
| (Example-3) | 0.4 | 920 ± 140 | | |
| X$_1$ = Br in the 2-position, | 0.1 | — | 1390 ± 130 | — |
| X$_2$ = p-Cl, R = CH$_2$COOH | 0.4 | | 1550 ± 60 | |
| [Example 8-(2)] | | | | |
| X = Cl in the 3-position, | 0.1 | — | 2280 ± 180 | — |
| X$_2$ = H, R = CH$_2$COOH, | 0.4 | | 2060 ± 60 | |
| [Example 6-(2)] | | | | |
| X$_1$ = Cl in the 3-position, | 0.1 | — | — | 3950 ± 120 |
| X$_2$ = p-Cl, R = COOH | 0.4 | | | 3110 ± 125 |
| (Example 5) | | | | |

As shown in Table-1, it is apparent that the drugs according to the present invention are as effective as or more effective than levamisole in remarkably increasing the number of the antibody-forming cells of the mice, that is, they have an outstanding immunostimulative activity.

(2) Effect on cellular immunity

The effect of the drugs on cellular immunity was estimated with an index of delayed-type hypersensitivity which is caused by injecting cells of sheep red blood as an antigen into the hind footpad of the mice (see the method described by P. H. Mackaness and T. E. Mille in the Journal of ExperimentalMedicine 139 1529–1539 (1974)).

A hundred million (10$^8$) sheep red blood cells suspended in 0.05 ml of phosphate-buffered saline were injected subcutaneously into the hind footpad of ICR mice (male, 12-weeks old) and then the mice were administered intraperitoneally with the drugs. Four days after the administration of the drugs, $10^8$ sheep red blood cells were injected subcutaneously into the hind footpad opposite to the one which was previously administered with antigen. Twenty-four hours after the injection, the thickness of the hind footpad was measured with a dial thickness gauge (GI type, manufactured by Ozaki Seisakusho) to determine the increase in thickness on the basis of the uninjected footpad. For the purpose of comparison, experiments were conducted with the mice which were not given the drugs and with those which were administered with levamisole instead of the drugs of the present invention. The results of these experiments are shown in Table 2, in which experiment-1 and -2 are quite the same except that the value of control are different.

arthritis, etc. These compounds are also expected to be employed as an anthelmintic for animals.

We claim:

1. Hexahydronaphth[1',2':4,5]imidazo[2,1-b]thiazoles of formula [I] and acid adducts thereof with an inorganic or organic acid

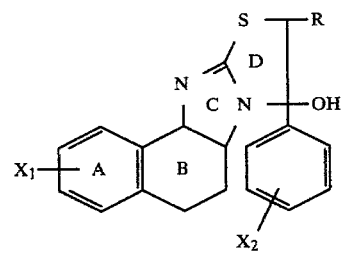

TABLE 2

| | Dosage (mg/mouse) | Increase in thickness of foot pad in mm | |
|---|---|---|---|
| | | Experiment-1 | Experiment-2 |
| No drug | — | 0.18 ± 0.10 | 0.37 ± 0.06 |
| Levamisole | 0.1 | 0.23 ± 0.07 | 0.48 ± 0.05 |
| | 0.4 | 0.37 ± 0.06 | 0.50 ± 0.05 |
| $X_1$ = H, $X_2$ = H, R = $CH_3$, M = HBr [Example 1-(2)] | 0.1 | 0.28 ± 0.05 | — |
| | 0.4 | 0.52 ± 0.05 | |
| $X_1$ = H, $X_2$ = p-Cl, R = $CH_2COOH$, M = HBr [Example 3] | 0.1 | 0.33 ± 0.04 | — |
| | 0.4 | 0.34 ± 0.03 | |
| $X_1$ = H, $X_2$ = H, R = H, M = none [Example 2-(2)] | 0.1 | 0.26 ± 0.05 | — |
| | 0.4 | 0.20 ± 0.04 | |
| $X_1$ = Br in the 2-position, $X_2$ = p-Cl, R = $CH_2COOH$, M = HBr [Example 8-(2)] | 0.1 | — | 0.48 ± 0.03 |
| | 0.4 | | 0.44 ± 0.02 |
| $X_1$ = F in the 3-position, $X_2$ = H, R = $CH_2COOH$, M = HBr [Example 6-(2)] | 0.1 | — | 0.49 ± 0.04 |
| | 0.4 | | 0.34 ± 0.02 |
| $X_1$ = Cl in the 3-position, $X_2$ = p-Cl, R = $CH_2COOH$, M = HBr (Example 5) | 0.1 | 0.40 ± 0.04 | — |
| | 0.4 | 0.27 ± 0.03 | |

It is evident from Table 2 that the drugs according to the present invention are as effective as or more effective than levamisole in increasing the thickness of the hind footpad of mice, in other words, in enhancing cellulose immunity.

Industrial Application

Since hexahydronaphth[1',2':4,5]imidazo [2,1-b]thiazole and its derivatives prepared according to the present invention have excellent immunostimulative or immunoregulatory activity, they are expected to be used as an immunotherapeutic agent for cancer or as a remedy for such autoimmune diseases as rheumatoid where $X_1$ and $X_2$ stand for hydrogen and halogen atoms; R represents a hydrogen atom, lower alkyl of 1 to 4 carbon atoms or carboxyl-substituted low alkyl given as —$(CH_2)_n COOH$ where n is an integral number of 1 to 3; A, B, C and D symbolize the rings respectively, and the configuration of rings B and C is trans.

2. Hexahydronaphth[1',2':4,5]imidazo[2,1-b]thiazole and adducts thereof according to claim 1, wherein R is a methyl in formula [I].

3. Hexahydronaphth[1',2':4,5]imidazo[2,1-b]thiazole and adducts thereof according to claim 1, wherein R is a carboxymethyl in formula [I].

* * * * *